United States Patent [19]
John

[11] Patent Number: 6,066,163
[45] Date of Patent: May 23, 2000

[54] ADAPTIVE BRAIN STIMULATION METHOD AND SYSTEM

[76] Inventor: Michael Sasha John, 1010 Orienta Ave., Mamaroneck, N.Y. 10543

[21] Appl. No.: 08/596,450

[22] Filed: Feb. 2, 1996

[51] Int. Cl.[7] .............................. A61N 1/32; A61N 1/18
[52] U.S. Cl. ................................. 607/45; 607/48; 607/62
[58] Field of Search ................................ 607/45, 48, 62, 607/65, 72

[56] References Cited

U.S. PATENT DOCUMENTS

| | | | |
|---|---|---|---|
| 3,850,161 | 11/1974 | Liss | 607/45 |
| 3,918,461 | 11/1975 | Cooper | 607/72 |
| 4,305,402 | 12/1981 | Katims | 607/62 |
| 4,505,275 | 3/1985 | Chen | 607/62 |
| 5,269,302 | 12/1993 | Swartz et al. | 607/45 |
| 5,540,734 | 7/1996 | Zabara | 607/72 |
| 5,571,150 | 11/1996 | Wernicke et al. | 607/72 |
| 5,611,350 | 3/1997 | John . | |
| 5,683,422 | 11/1997 | Rise . | |

*Primary Examiner*—William E. Kamm
*Assistant Examiner*—Carl H. Layno
*Attorney, Agent, or Firm*—Michael S. John

[57] ABSTRACT

An adaptive brain stimulation system and method is described which aids in the rehabilitation of patients from traumatic brain injury, coma, or other brain dysfunction. After a direct brain stimulator is implanted in a brain region of a patient, the patient is stimulated according to a set of stimulation parameters. A present state is measured and compared to a reference state by statistical and medically relevant criteria. The subsequent program of stimulation is dependent upon the outcome of the comparison. An adaptive brain stimulation and reinforcement system and method is also described in which a second area of the brain is stimulated when stimulation of the first brain area produces a desired effect, thereby reinforcing the prior response of the brain.

30 Claims, 4 Drawing Sheets

ADAPTIVE BRAIN STIMULATION METHOD AND SYSTEM

FIELD OF THE INVENTION

The invention relates generally to medical monitoring and medical resuscitative systems and methods and more specifically to an adaptive neutral stimulator system and method for the treatment of traumatic brain injury and the often resulting persistent vegetative state or "coma" or the treatment of other brain dysfunctions such as movement disorders. The system stimulates and modifies parameters of stimulation based upon the outcome of comparing the patient's present state with a reference state with the intention of improving the overall functional state of the patient.

DESCRIPTION OF PRIOR ART

The term "coma" is used to describe a human patient's state wherein the patient is unconscious and immobile and does not respond to intense sensory stimuli, for example, yelling. A "deep coma" occurs when this state lasts for more than 1 week. Although coma may result from several causes including drug reactions or cardiovascular stroke it is often due to head injury, for example, head trauma due to an automobile accident.

Historically, recovery from coma has been demonstrated primarily in laboratory animals. Early studies in cats showed that functional disconnection of the reticular formation from the rest of the central nervous system (CNS) resulted in a loss of consciousness, implicating this region as responsible for the state of CNS arousal. Subsequent research (Adametz, J H, Recovery of functioning in cats with rostral reticular lesions, J of Neurosurgery, 1959(16), Pp.85–97) showed that if the reticular region was destroyed in consecutive steps, rather than all at once, and the brain was given the opportunity to reorganize itself, the animals would not lose consciousness. A characteristic of the brain that enables it to respond to the insult that resulted in coma is neural plasticity which occurs when the functions of a damaged region of neural tissue is taken over by other areas that normally dud not previously play a role in that particular function. Since the brain can respond to traumatic injury by using such adaptive capacities as functional and structural reorganization, upregulation or downregulation of a neural response to an event, and the establishment of new functional and structural connections by means of collateral sprouting and compensatory synaptogenesis, patients are sometimes able to regain consciousness after being in a coma.

Recent evidence indicates that direct electrical stimulation of the human brain can be effective in the reversal of persistent vegetative state (PVS) resulting from traumatic injury or stroke (Hassler R, et al., EEG and clinical arousal induced by bilateral long-term stimulation of pallidal systems in traumatic vigil coma. Electroencephalogr Clin Neurophysiol. 1969 September; 27(7): 689–690. Cohadon F, et al, Deep cerebral stimulation in patients with post-traumatic vegetative state. Neurochirugie. 1993; 39(5): 281–292. Deliac P, et al., Electrophysiological development under thalamic stimulation of post-traumatic persistent vegetative states. Neurochirurgie. 1993; 39(5): 293–303. Cohadon F. et al., Recovery of motor function after severe traumatic coma. Scand J Rehabil Med Suppl. 1988; 17: 75–85. Kanno T, et al. Effects of dorsal column spinal cord stimulation (DCS) on reversibility of neuronal function—experience of treatment for vegetative states. Pacing Clin Electrophysiol. 1989 April; 12(4 PT 2): 733–738. Kanno T, et al. Neurostimulation for patients in vegetative status. Packing Clin Electrophysiol. 1987 January; 10(1 Pt 2): 207–208. Tsubokawa T, et al. Deep-brain stimulation in a persistent vegetative state; follow-up results and criteria for selection of candidates. Brain Inj. 1990 October; 4(4): 315–327. Katayama Y, et al. Coma induced by cholinergic activation of a restricted region in the pontine reticular formation—a model of reversible forms of coma. Neurol Med Chir (Tokyo). 1986 January; 26(1): 1–10.), or in improving motor control in patients with movement disorders such as Parkinson's Disease (Limousin P, et al., Effect of parkinsonian signs and symptoms of bilateral subthalamic nucleus stimulation. Lancet. 1995 January 14; 354(8942); 91–95. Limousin P, et al Bilateral subthalamic nucleus stimulation for sever Parkinson's disease. Mov disord. 1995 September; 10(5): 672–674. Pollak P, et al., External and implanted pumps for apomorphine infusion in parkinsonism. Acta Neurochir Suppl (Wien). 1993; 58–52. Pollak P, el al., Long-term effects of chronic stimulation of the ventral intermediate thalamic nucleus in different types of tremor. Adv. Neurol. 1993; 60; 408–413.). There is also evidence that electrophysiological (EEG or ERP), electromyographic (EMG), neurochemical (CSF metabolites), peripheral (circulating beta-endorphin levels), radiological (CT scan, MRI) and clinical (Pupillary Light Reflex, Glasgow Coma Scale) measures may aid in providing useful selection criteria for patients who may be likely to successfully respond to direct brain stimulation (DBS) treatment. These measures may also offer a means to monitor the efficiency of acute or chronic DBS treatment. Since there are 2,000,000 cases of traumatic brain injury each year in the United States, with a substantial percentage leading to a persistent vegetative state or "coma", successful coma treatment would be of great clinical utility, decreasing mortality and morbidity.

Instruments for direct electrical brain stimulation are currently available from several companies (Medtronics, Neuromed, Cochlear Corp. Advanced Bionics) These devices are in clinical use and often rely on systems chronically implanted into the brain or peripheral sites. U.S. Pat. No. 4,735,204 (referred to herein as "the '204 patent") describes a system for controlling a neural stimulation device that is implanted in the epidural space along the spine and which is used to block ascending pain signals in chronic pain. Since the amount of pain may change over time depending upon the patient's activity level or position, the '204 patent describes how the level of current supplied to an implanted stimulation electrode is modified, within certain acceptable limits, by the application of an externally applied magnetic means thereby avoiding a visit to a medical facility. In the '204 patent the optimal level of stimulation is chosen by the patient by a criterion where the patient again attains comfort. U.S. Pat. No. 5,342,409 describes a chronically implanted position responsive neurostimulator which is useful in the treatment of cases with chronic intractable pain, various movement disorders, and lack of bowel and bladder control, in which the stimulation parameters are programmed into a stimulation controllers by professional personnel via transcutaneous RF telemetry signal. U.S. Pat. No. 4,592,359 describes a multi-channel implantable neural stimulator which functions as an auditory prosthesis. The invention includes a transmitter and chronically implantable receiver and an efficient transmitted data format which both transmits data and induces a charge on the implanted stimulator.

While the existing art are of considerable medical utility, none of the described invention utilizes a systematic, statistical, and medically meaningful method for determining the stimulation parameters in order to optimize efficacy of stimuli to be ultimately used in treatment. Accordingly, it is the object of the adaptive brain stimulation (ABS) system and method of the present invention to greatly improve the treatment of central nervous system pathology such as coma by relying on statistically significant and medically meaningful criteria for choosing a specified program of stimulation.

It is a further object of the present invention to utilize an ABS that controls multiple stimulation devices that are implanted in a first brain region and a second brain region, and which stimulate these regions according to a set of parameters which produce functional or structural recovery which enables the patient to overcome unwanted effects resulting from traumatic brain injury, stroke, or brain disorder or disfunction.

SUMMARY OF THE INVENTION

An adaptive brain stimulation system and method is described which aids in the rehabilitation of patients from traumatic brain injury which has resulted in a persistent vegetative state, or other brain dysfunction. After a direct brain stimulator is implanted in a brain region of a patient, the patient is stimulated according to a set of stimulation parameters. A present state is measured and compared to a reference state. If the comparison meets a set of criteria, then the stimulation is producing a desired effect and a positive outcome is said to have occurred resulting in a continuation of stimulation according to a current set of stimulation parameters if, however, after a specified amount of time or number of attempts, the comparison fails to meet a set of criteria then new sets of stimulation parameters are selected and subsequently tested until a positive outcome again occurs.

In an alternative embodiment of the present invention, in the case of a positive outcome a second set of DBS's which is in another brain region may also be stimulated by a specified reinforcement schedule. If the second brain region is related to reward, then the brain is reinforced for producing a response that succeeds in meeting a criteria.

The ABS system is a feedback loop that provides stimulation to a patient based upon statistical and medial criteria. In actual practice the system includes electronics, sources of power, amplifiers, stimulators, and appropriate means for connection and communication between functionally related components. External components are under control of a personal computer (PC) device and internal components are controlled by micro-electronics. As is well known to those skilled in the art, and as is described in the above cited art, current technology can allow the ABS system to be almost completely implanted or it may have a relatively large number of its components located external to the patient. If the ABS is located internally it can contain both a communication means for sending and receiving signals to its external components and a long-lasting replaceable or rechargeable power supply which can be recharged via induction or by radio frequency transmission. Since the ABS system is a medical device, it must obviously meet patient safety standards by including protection of the patient from electrical surges and runaway feedback, and includes the necessary hardware and software subroutines to perform appropriate diagnostic checks to ensure correct functioning.

After the patient regains consciousness by returning from the coma or manifest an other desired improvement by recovering from a dysfunctional state, the ABS system can be implanted into a patient and aid in the subsequent maintenance of the normal state.

BRIEF DESCRIPTION OF THE DRAWINGS

For the purpose of illustrating the invention, there are shown in the accompanying drawings forms which are presently preferred, it being understood that the invention is not intended to be limited to the precise arrangements and instruments shown, and wherein.

DETAILED DESCRIPTION OF THE INVENTION

System Specification

Figure 1:
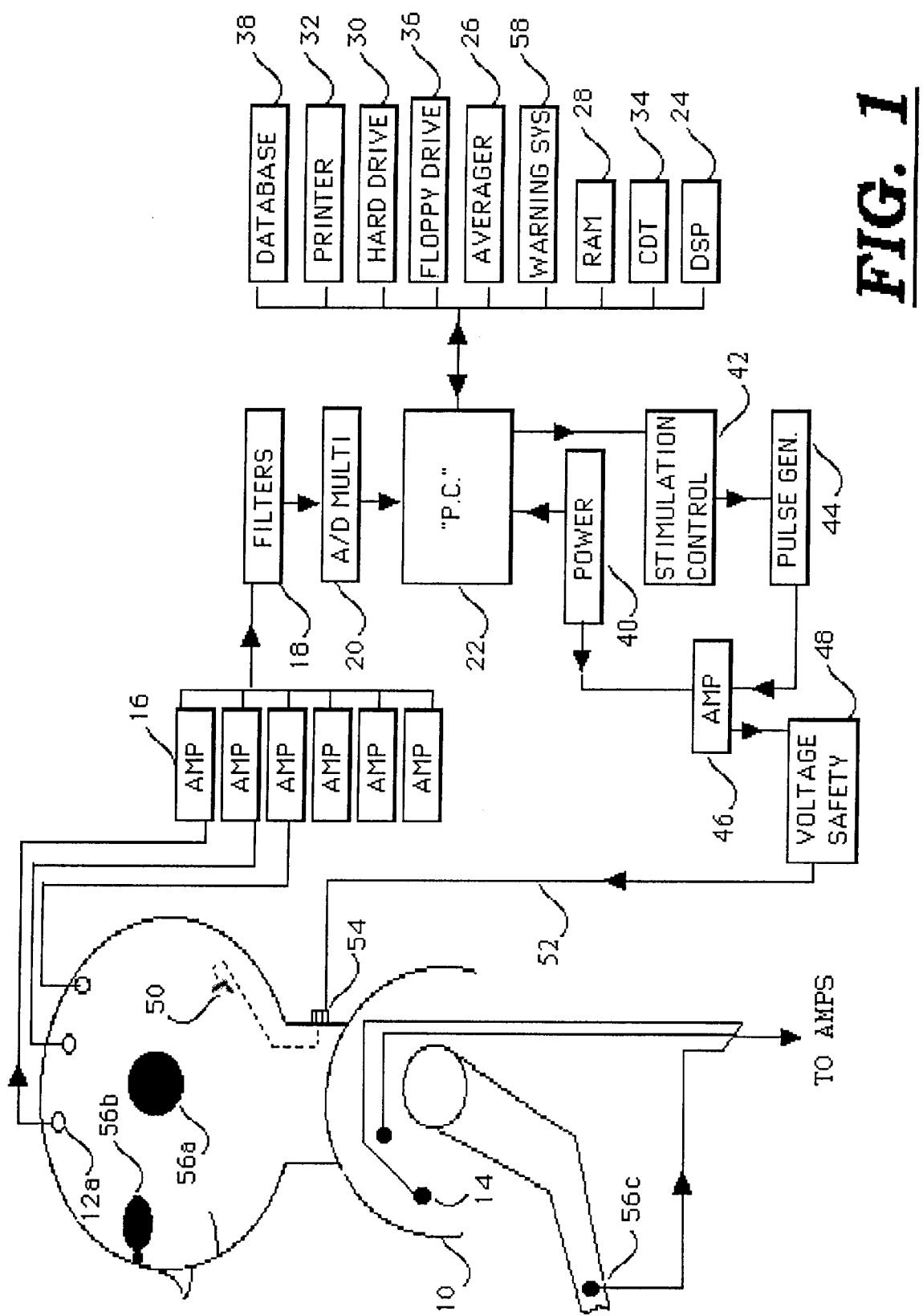
FIG. 1 is a block schematic drawing of the apparatus of the present invention.

Referring to FIG. 1, an embodiment of the ABS system of the present invention is shown and includes an electrophysiological monitor that measures signals from the brain or body of a patient 10 (e.g., EFG, EKG, EP or EMG) using EEG 12a, EKG 14 or EMG (not shown) electrodes and a conventional monitoring system including a set of amplifiers 16, filters 18, and an analogue-to-digital multiplexer (A/D multi) 20 that is incorporated into a circuit board that is removably located on the motherboard of personal computer 22 "PC". The PC computer contains hardware such as a digital signal processor (DSP) 24 and an averager 26, or the software equivalent of the these devices, so that the digitized values of the electrophysiological signals ("the data") can be analyzed in both the time and frequency domain. Both the raw and analyzed data are collected from the patient and stored in RAM 28 according to the normal operational needs and uses of the system. Data is stored on the hard drive 30 for long term storage. The raw and analyzed data can also be outputted to a printer 32, a display device such as a computer display terminal (CDT) 34, or a conventional storage device such as a floppy disk drive 36. The attending medical personnel can use the computer's keyboard and function keys to modify the display of the data and the stimulation parameters and stimulation treatment routines according to the desires and judgement of the attending medical personnel.

When the data is collected, it is compared to a set of reference values from a database 38 which contains a set of reference values that can include values previously obtained from the patient, values that the medical personnel have chosen, or values from an appropriate normal population. The ABS of the present invention then selects a set of stimulation parameters based upon this comparison and sends these parameters to a stimulation system. The stimulation system, which may be incorporated into and under control of the PC, includes a medically approved power source/power transformer 40, a stimulation control device 42 that guides the stimulation according to a set of stimulation parameters, and a pulse generator 44, under the direction of the stimulation control device, that generates an electrical pulse train. The pulse train is sent through both an output amplifier 46 and a safety voltage control circuit 48 before it is delivered to the implanted direct brain stimulator (DBS) 50. The control circuit is electrically connected to the DBS by medically approved insulated conducting wires 52 and connection plugs 54 which are arranged to form a functional transdermal electrical connection.

Alternatively, rather than relying on a physical transdermal connection, internally implanted DBS's can be programmed by or powered from external sources, for example by magnetic induction or radio-frequency charged super capacitors. Additionally, the components that measure and compare the present state can be incorporated into an implanted hybrid microchip and the recording electrodes may be placed in the dura on the skull in the brain, or in/on muscle.

The ABS system and method also contains devices for auditory stimulation such as headphones 56a, for visual stimulation such as LED goggles 56b, and for somatosensory stimulation such as a tactile stimulator 56c that is attached to the wrist or fingers of the subject, all of which are controlled and powered by the PC. These stimulation device enable the generation of auditory, visual, and somatosensory transient evoked potentials and steady state potentials that can be recorded from the EEG electrodes.

The ABS also monitors autonomic nervous system measures (EKG, ECG, blood pressure) to detect positive effects of stimulation as well as to ensure that the stimulation is not adversely affecting vital functions. If a comparison of vital signs with the stored reference values indicates that the patient has become adversely affected then stimulation is halted and a warning system 58 alerts attending medical personnel.

Electrode Implantation and Setting Stimulation Parameters

The stimulation should be directed at appropriately selected brain regions such as thalamic nuclei including the centre median or the intralaminar nuclei, the subthalamic nucleus or striatal structures, the dorsal columns, or selected regions of the spinal cord that project to appropriate reticular, thalamic, and cortical areas. Implantation of the stimulation devices can include a diagnostic phase in which cortical or subcortical areas are stimulated by the medical personnel and sites which produce increases in electrical activation, autonomic indices, or CNS metabolism can be selected as potential sites of stimulation. Appropriate sites of activation can be determined by functional and structural imaging technology such as PET, FMRI, SPECT, EEG, EP, MEG, and by pharmacological testing such as assays of CSF fluid metabolite levels. Since EEG or MEG are currently the least expensive techniques appropriate for monitoring the overall state of the CNS on an ongoing basis, they are the most obvious measures to be used as indicators of CNS state during the treatment process. Subsequent periodic diagnostic checks may be done at various times during the treatment any of the above mentioned imaging technologies.

After the simulation device or devices are implanted, medical personnel can determine several stimulation parameters which result in improvement in the condition of the patient. These stimulation parameters include those that are described in U.S. Pat. Nos. 4,702,254 and 4,592,359 such as pulse amplitude or current, pulse width, pulse time, pulse frequency, pulse train duration, rate of stimulation, as well as other parameters such as inter-train interval, pulse shape, DC offset, bursting or non-bursting mode, and AM or FM stimulation mode. After a set of advantageous stimulation parameters have been discovered, these can be programmed into the stimulator control. Advantageous stimulation parameters are those which cause a desired shift in the present state compared to a reference state. The ABS is also able to function in an "automatic stimulation search and selection" mode in which a series of stimulation parameter combinations are automatically chosen and tested in a regular or random manner and parameters which cause an improvement in the patients condition are stored as a set of possible alternative parameters.

Treatment Mode 1.

After a first set of parameters is chosen by either of the described automatic or manual methods or by a combination of the two methods, the device is set to begin a stimulation regimen.

Figure 2:
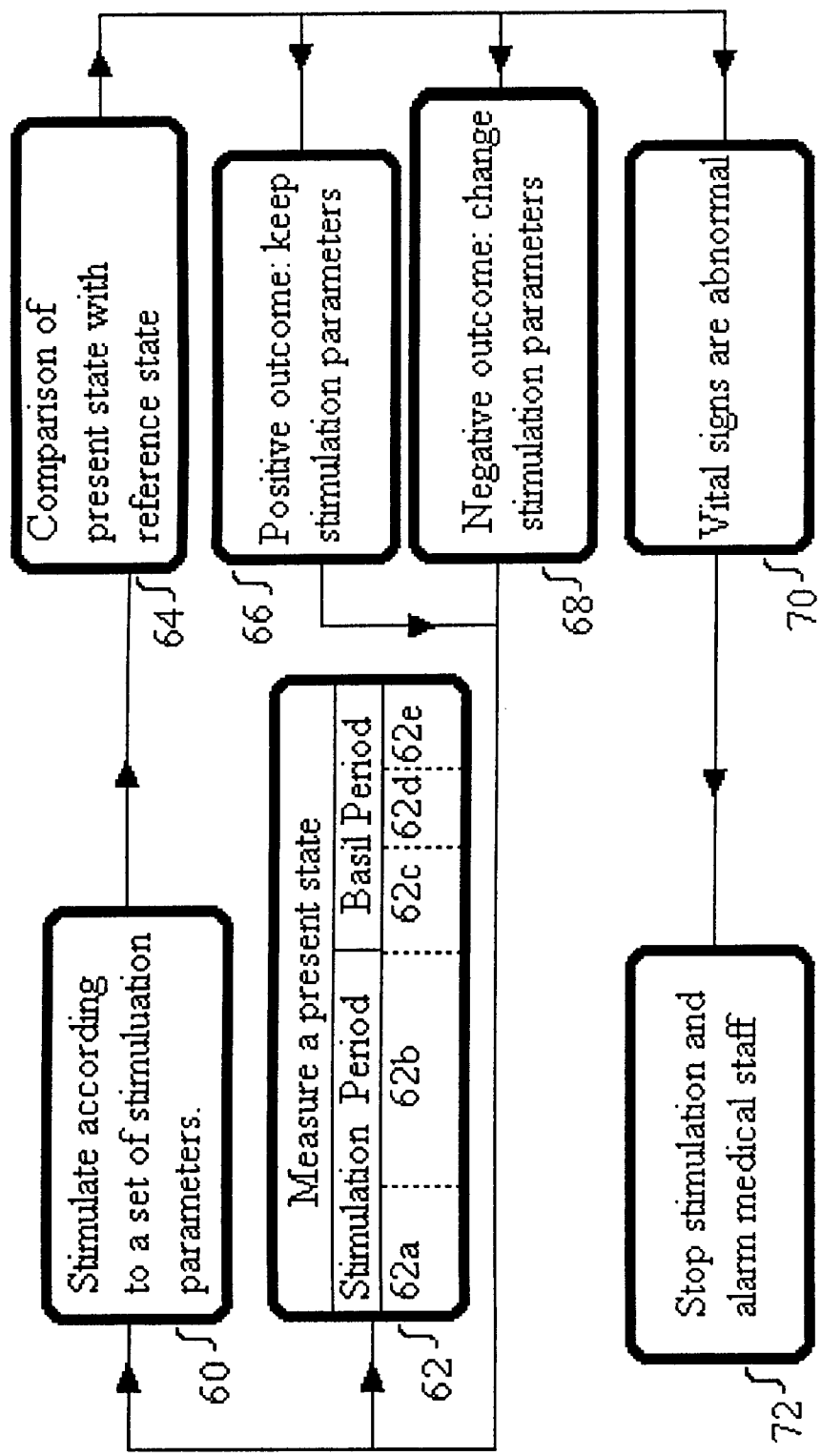
FIG. 2 is a schematic representation of an adaptive brain stimulation method, performing in accordance with the principles of the present invention and showing the manner in which the stimulation is modified so that the patient receives safe and efficient treatment.

As shown in FIG. 2, the first stimulation 60 occurs and the subsequent state of the subject is measured 62. The current state (a "state" is defined as a set of measures obtained from the patient), is then compared to a reference state 64, which may be a past state or a weighted set of past states, or a normative mean value of such signals for an appropriate age matched population, possibly taking medical condition and other relevant factors such as medications into account. The comparison can lead to either a positive outcome subroutine 66 or negative outcome subroutine 68. A positive outcome results when the current state meets a set of criteria, indicating an improvement of the patient's condition, e.g., the clinical signs or monitored state indicate that the patient's brain state is moving toward a target state. When a positive outcome occurs, the set of stimulation parameters is not changed and stimulation is repeated.

If after a specified interval or number of stimulations the current state fails to meet the comparison criteria relative to a reference state, then a negative outcome has occurred. In the occurrence of a negative outcome, before subsequent stimulation takes place, the stimulation parameters are changed and the present state is again compared to a reference state, until the comparator indicates that favorable mode of stimulation has again been achieved. In the case of a negative outcome, the selection of subsequent stimulus parameter can be based upon some specific program of stimulation, or based upon a program that relies on a methodical permutation of increasing or decreasing set of values, or upon an algorithm that utilizes past successful parameters and discriminates against unsuccessful parameters for that subject, or upon values in a database based computed from a normative population, or upon a random or quasi-random strategy.

The ABS method and system can also include monitoring of vital functions (EKG, blood pressure, respiration) to detect positive effects of stimulation as well as to ensure that vital functions are not adversely affected by brain stimulation. If a current program of stimulation begins to affect vital signs adversely 70, stimulation is discontinued 72 until an appropriately trained medical person evaluates the medical state of the patient and decides on a new program of stimulation.

A present state of a patient can be divided into a "stimulation period" and a "post-stimulus period." The stimulation period is defined as a period that is in, or is temporally close to, the period in which stimulation occurs, for example from stimulation onset until stimulation offset or lasting up to, for example, 1 second post-stimulus 62c. The stimulation period may also be sub-divided into two or more smaller sections of interest 62a, 62b. The "post-stimulus period" may similarly be a single period or may be divided into two or more sub-periods 62c, 62d, 62e which begin after the stimulation period and last until the next stimulation period. The post-stimulus period may be characterized by complete cessation of stimulation or by a relatively decreased level of stimulation compared to the stimulator state. Stimulation may also be continuous. Comparison of the current state with a reference state may entail a comparison of a current state concurrent with an ongoing DBS or the subsequent post-stimulus period or a fraction of that interval relative to an appropriate reference period. When the neural response to the stimulation is sufficiently large, the present state during the stimulation period can be measured even by the EEG scalp electrodes. Since the ABS system applies a discrete electrical pulse train to the brain, it should be obvious to those skilled in the art that when the present state contains a sufficiently large phase-locked EEG oscillation that was elicited by the stimulation, it can be evaluated as an evoked potential with constituent components having peak amplitudes and latencies.

The comparison of the selected current state to the appropriate reference state utilizes statistical criteria which may be computed on raw or Z-transformed data and which may include multiple t-tests to compare the mean values of the variables in each of the states, or computation of the F-ratio to compare the variance of variables in each of the states, or computation of an appropriate multivariate measure.

For example, the variance $\sigma^2$ of any variable x can be written as $\sigma^2(x)=(\Sigma x^2/n)-(\Sigma x/n)^2$ where n equals the number of measurements. The distribution of amplitudes at any frequency in the EEG is known to be Gaussian, with a mean value equal to zero, therefore $(\Sigma x/n) \cong 0$. Thus, the variance of the EEG at any frequency can be considered to be simply $\sigma^2(x)=(\Sigma x^2/n)$, in other words equal to the mean power. The ratio of power, $(P_T)$, in any test period to the power, (Pc), in a reference or control period will be $P_T/P_C=\sigma_T^2/\sigma_C^2$. This expression can be treated as a F ratio yielded by a one way analysis of variance, with degrees of freedom (a−1)·n where a=the number of conditions compared and n=the number of measurements. This F value can be converted to a measurement of probability by using the Fischer Z transform. [Note: In order to achieve a Gaussian distribution, the values of power can be log transformed prior to computation of the Z score.]

In view of the above explanation, it is evident that the effect of brain stimulation upon any measurement of power in the frequency domain of the EEG power spectrum or upon the power in any latency interval of an EP analysis epoch can be evaluated statistically by using the ratio of the Power at a specified time after a period of brain stimulation, $(P_A)$ to the Power during a reference state, before stimulation, $(P_B)$. Since normative population data, $(P_N)$, at any age are available, for both the resting EEG power spectrum as well as the EP waveshape to somatosensory or auditory stimulation across the latency epoch, the estimate of the statistical probability that a given type of stimulation has altered the EEG or the EP can be assessed in order to ascertain whether the brain of a patient displays an EEG or EP which is more normal after than before the occurrence of stimulation. That is, if $(P_N/P_A)<(P_N/P_B)$, then the brain state after stimulation is closer to the normal state than the state that was present before stimulation. [Note: the criterion used in this expression is that the power of the reference measure in the normal state is expected to be greater than in the patient, as would usually be the case for the alpha or beta band in coma. Were delta or theta used as the criterion variable, the sign of the inequality would reverse.] $P_N$ may also be based on the value of a parameter of the EEG or a component of latency interval of the EP that the medical personnel have selected as a goal, or optimum value to be reached by that patient, or which is a self-norm of the subject during a desired state that was previously identified.

It is obvious to those skilled in the art that this criteria can be applied in the multivariate case. Multivariate composites or Mahalanobis distances, taking into account the covariance among several measures may also be thus assessed. A multivariate index can be computed using the equation $\Sigma C_i(P_{iN}/P_{iA})<\Sigma C_i(P_{iN}/P_{iB})$, where $P_i$ is a quantitative measure of data that is obtained from any of the set of electrodes (e.g., alpha power at posterior sites, or power of an EP at a specified latency interval), $C_i$ is an appropriately chosen weighting coefficient, and the appropriate transformations are done so that the inequality is medically meaningful (e.g., a negative one (−1), or $1/P_i$ is used when appropriate). The choice of using a value other than 1 for any $C_i$ is often made based upon a medically relevant criteria as will be described.

Alternatively, since the mean values, M, and the standard deviations, σ, of the power in the resting EEG are known for the delta (1.5–3.5 Hz), theta (3.5–7.5 Hz), alpha (7.5–12.5 Hz), and beta (12.5–20 Hz) bands at every scalp electrode position in the International 10/20 System for normal individuals at any age, the values of Z can be calculated for each of these frequency bands, where Z=[M−P]/σ and M=normal mean values for the age of the patient, P=patient values of present state, σ=standard deviation of the normal distribution. Improvement after stimulation or infusion is defined as decreased positive values of Z for delta and/or theta (diminution of excesses) and decreased negative values of Z for alpha and/or beta (diminution of deficits). M and σ can also be calculated for a quantitative measure (e.g., mean alpha power) or a set of measures (e.g. alpha/theta at electrode P3+alpha/theta at electrode P4) that are computed from physiological data that are collected from the patient prior to stimulation or during an alternatively defined baseline period, and changes in Z can be evaluated relative to the changes desired by the attending medical personnel or from a database constructed from previous positive outcomes. Similar to the EEG analysis, evaluation can also be carried out for the power in the epochs between 0.5 and 6.0 milliseconds of the averaged brainstem auditory evoked potentials to clicks and between 1 and 14, between 1 and 14, between 14 and 22, and between 22 and 50 ms of the averaged evoked potential to dorsal spinal column or thalamic stimulation, or stimuli delivered to the median or ulnar nerve at the wrist. Increased power in those latency intervals after stimulation indicates better transmission of sensory information to the higher structures of the brain.

Although normally only a few electrode leads will be used in treatment, a large set of scalp leads may be used during the early stages of treatment. Z can be made multivariate using the equation $\Sigma C_{ik} \cdot Z_{ik}$ where Z is a matrix of Z scores comprised of I rows for each electrode, k columns for each parameter computed on the data obtained at that electrode, and C is a matrix of coefficients that corresponds to the elements in Z. In order to decrease the size of Z and reduce the amount of redundant data contained within that matrix, M and σ can also be computed across a reference set of samples of factor scores of factors that are obtained from a principle component analysis (PCA) of spatial (EEG) or spatial-temporal (EP) data that is recorded from all the electrodes on the head (e.g., OCA may be computed across the head for EEG measures such as relative power, coherence, or power at a given latency in the case of an EP). In this case the medically meaningful Z index may be obtained by computing the deviation $Z^*=C_i|\Sigma Z_i^2|^{1/2}$, where $Z^*$ is the length of the n-dimensional vector of factor Z-scores, and $C_i$ are the corresponding weighting coefficients. Since PCA performed on data from a present state would produce a different set of factors than if the PCA were computed on data from a reference state, the factors Z-scores for the reference state and the present state should be based upon the factors generated from reference state data.

It should be obvious to those skilled in the art that since $C_i$ is medically relevant, it can be automatically changed during the course of the day according to the circadian changes which are evident in a patient. It should also be evident that Z may also be computed for various other biological processes that are sensed by a set of sensors that are either implanted in or attached to the patient, such as movement or EMG sensors in the case of a Parkinsonian tremor, or measures obtained from implanted electrodes, etc. Z may also be computed on subjective measures such as pain or discomfort. During a period of subjective assessment, the patient provides subjective ratings along, for example, at least one 10 point scale where 1 and 10 are at opposite ends along some scale of sensation (e.g., pain-lack of pain, alert-drowsy, focused-dizzy).

A series of relevant publications and patents in the name of Dr. E Roy John relate to the field of EEG "neurometrics", which evaluates Quantitative EEG measurements relative to normative data. Generally, a subject's analog brain waves at the microvolt level are amplified, separated from artifact caused by non-brain sources of electrical activity, and converted to digital data. The data are then analyzed in a computer system to extract numerical descriptions which are compared to a set of norms which can be either the subject's own prior data (self-norm) or can be a group of normal subjects of the same age (population norm). Such an analysis can quantify any deviation of the activity of any brain region from normal values.

A computer system instrument that is based on these principles is the "Spectrum 32" (Caldwell Instruments, Washington). That instrument is not suitable for adaptive brain stimulation because it is not configured to obtain signals from implanted sensors and is not configured to provide stimulation to the patient based upon a set of criteria. Some of the aforementioned patents related to neurometrics and the Spectrum 32 are U.S. Pat. Nos. 4,279,258; 4,846,190; 4,913,160; 5,083,571 and 5,287,859.

If one EEG electrode is used by the ABS system and is placed at a preferred electrode site such as "CZ" according to the International 10–20 system of electrode placement as is known to those skilled in the art, then at least one of the following variables are used in the computation of a present state: absolute or relative power in the conventionally defined delta, theta, alpha, and beta frequency bands, or a set of user specified bands. When additional pairs of homologous electrode locations are used from the right and left hemispheres of head (e.g., F3 vs F4 and P3 v P4) then measures of left-right and anterior-posterior correlation or coherence are also available to be used in the computation of the present state.

In addition to EEG, evoked responses (EP's) are generated by means of sensory stimulation. Automatic detection and evaluation of EP's can be accomplished by many statistical methods. For example, digital filtering, peak detection and latency estimates, or measures of spectral power in a latency interval can be compared to normative distributions, values obtained earlier from the patient, or other appropriate reference set. Significant changes in the shape of the EP's can be automatically measured by collecting a series of single EP's and performing a Principle Component Analysis on the data which yields a series of eigenvectors that account for independent sources of variance in the data. By evaluation of the factor scores by weighting coefficients required to reconstruct the EP, the ABS can automatically detect changes in the EP. Alternatively, as is well known to those in the art, many automatic EP programs will find the amplitude, latency, or power of an EP or averaged EP, so that evaluation of the data by a trained operator is not necessary.

Treatment Mode 1.

Figure 3:
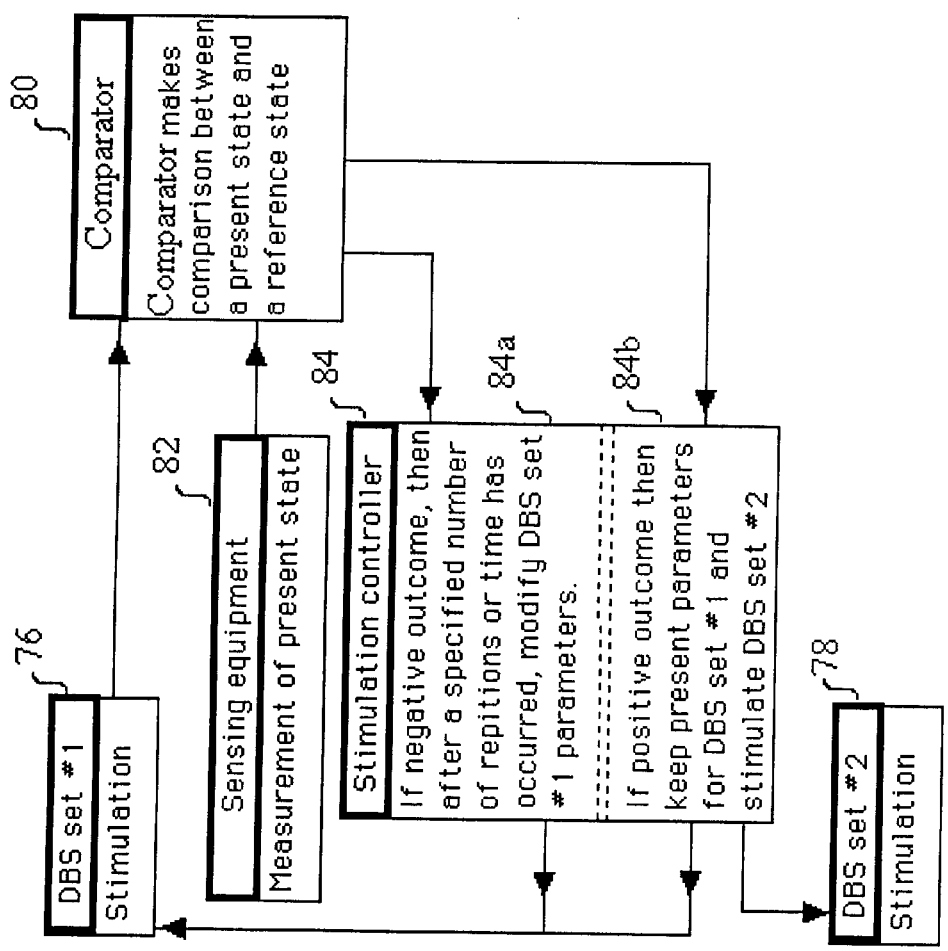
FIG. 3 is a schematic representation of an adaptive brain stimulation system and method, the embodiment shown illustrating how two brain regions can be incorporated into the treatment.

The treatment of brain disfunctions or disorders, such as coma, stroke, or epilepsy, or movement disorders the ABS system can further be enhanced by incorporating an approach which includes multiple brain regions. In an alternative embodiment of the ABS system and method, at least two stimulation sites are utilized to achieve beneficial effects, as is shown in FIG. 3. In accordance with the figure, stimulation set #1 76 contains at least 1 DBS device which stimulates a first brain region. Additionally, a second brain area is stimulated by stimulation set #2 78 which also contains at least 1 DBS device. The parameters of stimulation set #1 are determined by evaluation with comparator 80, which makes a comparison of a present state in relation to a chosen reference state. The present state is estimated using values measured by at least one sensor 82 which is implanted and maintains transdermal electrical connectivity by means of connection apparatus 54, or which is a scalp electrode 12a (FIG. 1). After the activation of stimulation set #1, two classes of stimulation cycles may occur. In cycle #1 patient's present state fails to meet a specified criterion relative compared to a reference state, even after a specified time interval or number (N) of repetitions. When cycle #1 84a occurs, new parameters are selected by the stimulation controller 84 and stimulation of DBS set #1 is repeated.

Alternatively, in cycle #2 84b, stimulation of DBS set #1 causes the patient's present state to meet specified criteria relative to a reference state. In this case, within a predetermined number of milliseconds after a positive outcome of the comparison, a paired stimulus is delivered by DBS set #2 to the second brain region according to a specified set of parameters that control the stimulation of DBS set #2. This reinforcement may be regular or aperiodic. The pairing between DBS #1 and DBS #2 78 continues until DBS #1 fails to produce the desired results and cycle #1 again occurs. The stimulation parameters that are used on DBS set #2 can be modified to create the optimal desired neural effect by relying upon the search methods previously described for the ABS system and method, used with a single brain region.

Figure 4:
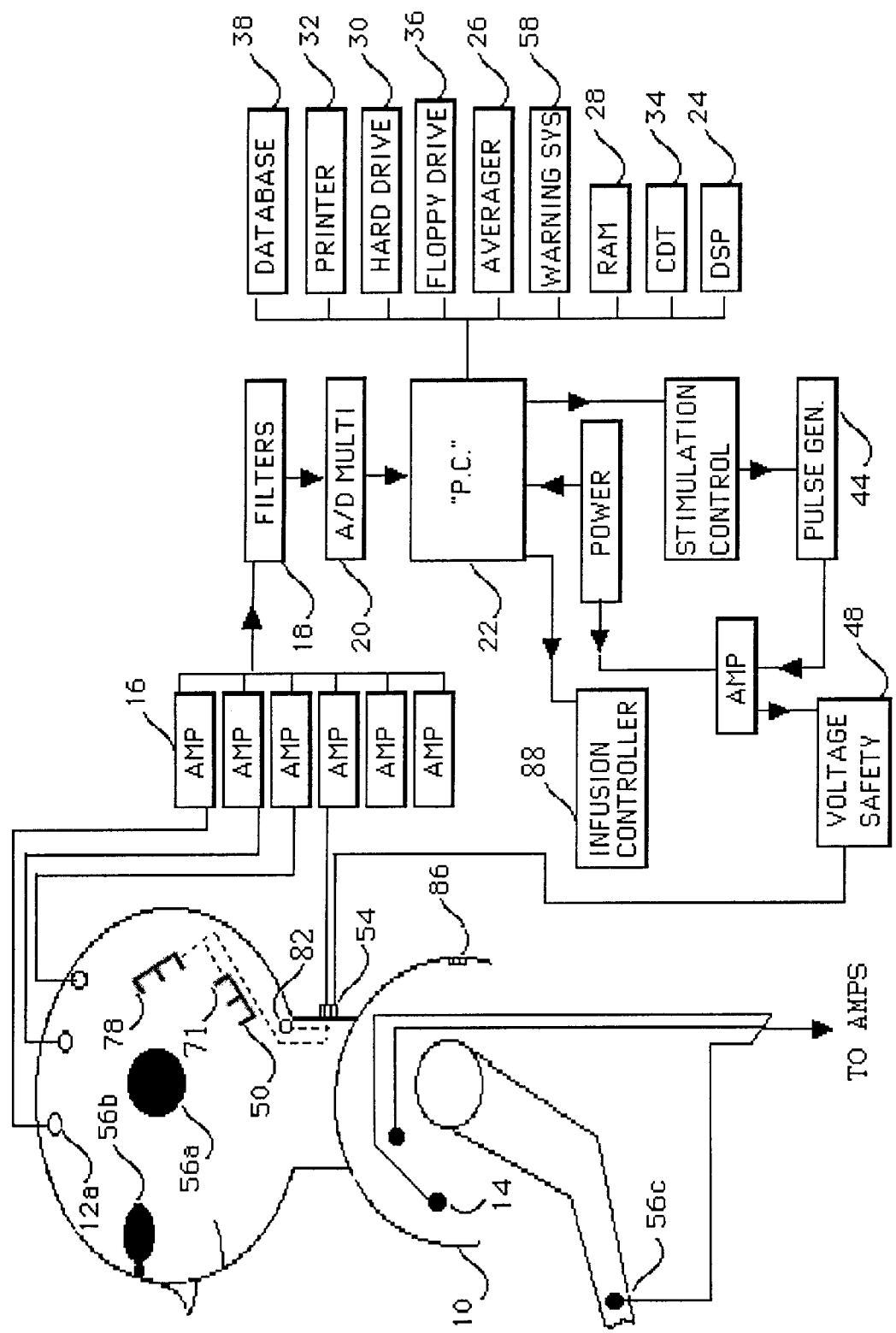
FIG. 4 shows another embodiment of the apparatus including a reservoir infusion apparatus (R.I.A), multiple electrodes, and an infusion controller.

While FIG. 4 shows all of the components found in FIG. 1 several additional features are shown here. In addition to a scalp electrode 12a, an implanted sensor electrode 82 is shown. Sensor 82 obtains physiological data that is sent to the PC 22 and used in the computation of a present or reference state. The single DBS 50, is not part of DBS set #1 71 which contains multiple DBS's. DBS set #2 78, is shown and illustrates that several DBS may be used on multiple areas of the central nervous systems. In DBS set #1 and DBS set #2, electrical stimulation can be replaced by or, work in conjunction with pharmacological stimulation which is achieved by a reservoir and infusion apparatus (R.I.A) 86 and infusion controller 88. In one embodiment of the invention, the infusion controller can be configured to act as a reservoir when it is physically connected to the R.I.A. In the illustrated embodiment, the infusion controller communicates with the RIA by telemetry such as is done in the case of implantable micro-infusion pumps that dispense insulin. The R.I.A. can provide a supply of pharmacological antagonists, or agonists such as psycho stimulants which can move the brain or an area of the brain into a more active state, or provide a supply of therapeutic agents such as neurotropic substances that will work either independently or in conjunction with the electrical stimulation to produce beneficial results. The substances can be transported to effective sites by means of a canal system or micro catheter system. For example, when used with a catheter in laboratory research, ALZET™ osmotic micro-pumps have delivered agents into the venous or arterial circulation, or target delivery to specific tissues or organs. ALZET™ pumps have been widely used to infuse agents into the brain. Targeted delivery techniques allow drug levels to be maintained locally, ensuring that effective levels are maintained in the desired target tissue. Targeted infusion can minimize unwanted systemic effects distant from the site of action. Since micro infusion pumps which are small enough to fit on a silicon chip are presently being designed, local injection of these substances by intracranial or pericranial micro infusion pumps is a preferred embodiment. The Alzet Brain Infusion Kit™ by ALZA corp. Could be used in some instances. While implantable pumps currently only have about a 1 month reservoir, for more prolonged delivery, pumps may be serially implanted with no ill effects. Although osmotic pumps offer many advantages, they currently release their contents at a constant rate. Therefore in the case of non-continuous pharmacological stimulation, a control means would have to be used. While the RIA and related infusion control can be a completely implanted device, the RIA could maintain functional connectivity, through the connection plugs 54, to an infusion controller 88, which can be powered by and in communication with the PC 22.

If DBS set #2 is located in an area of the central nervous system (CNS) that is related to the non-specific reward system, then by stimulating DBS set #2 just after the occurrence of a desired present state the CNS is rewarded for generating a desired brain response. Several lines of evidence, which have appeared in reports in the relevant medical and scientific literature and which are commonly known to those skilled in the art, indicate that contingent stimulation of the dopamine (DA) system can reinforce a particular pattern of neuronal firing that occurred previously. Paired DA reinforcement reliably elicits a multitude of desired responses from an organism and excitation of the meso-limbic DA system is functionally identical with reinforcement in classical behavioral and neurophysiological models. For example, laboratory animals will choose to press levers instead of eating, even to the point of starvation, when lever presses are rewarded by an injection of DA directly into the brain. Further, on a cellular level, there is evidence (Olds J. Hypothalamic Substrates of Reward, Physiological Review, 42: 544–604, 1962) that biofeedback which involves DBS or microinjection of a region appropriate neurotransmitter in such brain regions as the ventral tegmental area, the hypothalamus, or nucleus accumbens, can successfully increase the frequency and/or intensity of any arbitrary reinforced event or behavior which can be controlled by the brain. By stimulating the release of a neurotransmitter or of afferent input when the brain activity of a present state yields a desirable outcome relative to a reference state, the ABS system and method can reinforce the brain for entering a desired state.

When DBS set #2 is located in an area of the central nervous system (CNS) not related to the non-specific reward system, pairing DBS #1 and DBS #2 still produces beneficial effects. Paired stimulation of separate brain regions strengthens connections between these regions. The fact that appropriately paired stimulation increases and reinforces both functional and structural connectivity between the stimulated brain regions is the basis of several neurophysiological models of long term potentiation (LTP), which is the neural process assumed to be essential for storage of memory (Kandel and Schwartz, 1993). Although LTP was originally shown in the hippocampus, it has since been shown to occur in many other regions of the brain. Stimulation of a neuroanatomical circuit also aids in brain compensation for a traumatic injury, which includes collateral sprouting, compensatory synaptogenesis, and cortical reorganization.

When trauma causes injury or destruction to a region of the CNS, the brain is able to reorganize ineffective or severed pathways as adjacent areas develop new connections. Compensatory responses occur both more readily and more rapidly with stimulation of relevant brain areas. Patients who have lost their ability to walk showed recover from this injury by reorganizing CNS connections rostral to brainstem, but only when they were forced to practice walking on a specialized treadmill (Dobkin B H., Neuroplasticity, Key to recovery after central nervous system injury. West J Med. 1993 July; 159(1): 56–60.). Practice has also be shown to be crucial to recovery of function in patients with cortical blindness (Zihl J. Recovery of visual functions in patients with cerebral blindness. Effect of specific practice with saccadic localization. Exp Brain Res. 1981; 44(2): 159–169.).

In coma, the opportunity for stimulation-assisted compensatory responses by the CNS is diminished because the brain is in a relatively inactive state. By concurrently stimulating 2 or more areas of the brain such as the reticular system and the thalamus, or the motor cortex and sensory or association areas (John, Mechanisms of Memory, 1967) the functional connection between these 2 regions can be strengthened. Further, in addition to contiguity, by concurrent stimulation including a reward region, such as the nucleus accumbens, the brain might enhance communication between any two regions.

Although DBS set #1 may be only one DBS device, in an alternative embodiment of the present invention DBS set #1 may include multiple DBS's, each of which may be governed by an independent set of stimulation parameters including onset and offset times. The stimulation parameters can include relative latency or polarity values, where the "latency" of a given DBS is defined in relation to some separate DBS. Although the DBS's will usually be bipolar in structure, having a relative anode and cathode between which the current travels, and might be concentric bipolar electrodes because these are designed to optimally stimulate a specific region, separate DBS's can be given alternating and opposite relative polarities so that current travels between them and creates a more diffuse field of activation.

One advantage of using multiple stimulation devices is that several areas that send afferents to a target brain region can be stimulated simultaneously or in sequence, increasing the probability of activation of a target area. An alternative method of using a DBS set with multiple stimulators uses stimulators at various sites along a functional neuroanatomical circuit. These DBS's can be stimulated at relative latencies that would approximate or "mimic" normal neural transmission along the circuit.

DBS's can consist of implanted electrodes or stimulating devices which may be active or passive and which may be connected to distal devices or may be entirely self-contained. Further, instead of electrical stimulation, stimulation can utilize pharmacological means such as systemic injection or local microinjection of psychostimulants (amphetamine) or other and functional agonists or antagonists which can be routed directly into a specific brain area or into a lateral ventricle. The injectable mediums can be stored at a distal site adjacent to other implantable devices and can be connected to the release site by a subcutaneous canal system. The release of the substance can be under the control of a central processor containing the required analytical electronics and a storing, pumping, or other dispensing means. Further, substances such as psychostimulants can be introduced into the patients by intravenous infusion, direct application to the nasal mucosa, or by infusion of the substance into the lateral ventricle, such as from an Ommaya sack reservoir before a period of electrical stimulation, increasing the likelihood of CNS response. Diffusion from a stored receptacle such as an Ommaya reservoir can be through a canal system that relies on passive diffusion or the flow may be more strictly regulated in terms of time and amount of released material by micro-pump systems and control means which can be located external to the CNS or to the patient, and in communication with the comparator.

Additionally, both electrical and pharmacological stimulation can be used together to further improve the patients condition. In one application, infusion of a substance intrinsically excitatory to a particular region is made contingent upon a specific pattern of cellular firing or upon an increase of a specific frequency in the EEG. Local administration of a neurotransmitter contingent upon a particular firing pattern increases the chances for subsequent repetition of this pattern. Thus, linking the infusion of a region-appropriate substance such as norepinephrine into the reticular region to a state of increased excitability should facilitate the probability of an increase in increase in subsequent firing rates.

Stimulation parameters can also include conditional criteria, the result of a logical operation performed upon a condition which results in a positive or negative outcome. As with the previously defined statistical and medically relevant criteria, in the case of conditional criteria only when a positive outcome occurs does stimulation take place. Additionally, like the other parameters, conditional criteria may be set independently for different stimulators. Conditional criteria are additional parameters such as time since last stimulation, time of day, etc., and can be designed so that stimulation occurs only at certain stimulators under specified conditions. Conditional criteria may be advantageous for several reasons. For example, if the comparison between a present state and a reference state yields a sustained positive outcome and DBS stimulation set #2 is located in nucleus accumbens, then continuous stimulation of this area could lead to long term elevated neurotransmitter levels (such as DA) and receptor desensitization. By including a conditional criterion which requires that a specified amount of time elapsed since the last stimulation, problems such as receptor desensitization are avoided. Alternatively, conditional criteria can be set so if repeated periods of stimulation have recently occurred, subsequent additional stimulation will occur only when the comparison of present state with reference state is more than an relatively larger pre-selected or incremental value.

Additionally, during the period of treatment, measures such as temperature can provide a means of detecting either regular or irregular occurrences of circadian or ultradian rhythmicity. In many cases of coma, a detectable sleep/wake cycle does exist. If such cycles approximate natural circadian rhythmicity, then the conditional parameters can be set so that stimulation occurs only during the more active state. Stimulation can be set to reinforce present or emerging circadian cycles and not to occur during an inappropriate chronobiological state, such as periods which might suggest sleep or less active states.

When brain or body state is measured in a multi-sensor embodiment of the ABS, analysis of measures used to define the present state can include analysis in the time domain, such as correlation or covariation between sensors. Analysis of measures can entail automated or manual evaluation of the components of the specific neural response to the stimulation known as an evoked potential (EP). The analysis of the EEG or EP data may be in the time or the frequency domain and can include measures of absolute power, relative power, mean frequency, symmetry or coherence, for a specified conventional frequency bands or a set of user defined bands or measures of waveshape or measures of power in early versus later latency intervals.

Since different types of brain trauma, medical condition, or medication could produce variability in the values detected by the sensors, a database can e provided which adjusts statistical response criteria to be medically meaningful. The comparison between present and past state can be modified based upon factors including: site and number of recording electrodes and stimulators, response to various stimulus parameters, medication, response selection and multiple montage criteria for various brain injuries. Supplementary to a reference database, individualized comparison criteria can obviously be set and modified by the attending professional personnel. Medically relevant criteria are important to ensure efficient and effective treatment. For example, if a brain injury caused a lateralized bias in damage, the comparison of present state to reference state is modified so that any improvement on the less damaged side is weighted more heavily than the damaged side, as that side is more likely to recover more quickly. Without weighting the measured variables according to medically relevant criteria, a relevant change in a small region of a brain that may be detected by only one electrode might not reach significance since when its value is averaged with the other electrodes it is less likely to reach significance.

In addition to the previously described types of direct electrical brain stimulation, stimulation of all five senses, both separately and in combination, has been shown to be effective in decreasing the time spent in coma (Sosnowski C, et al. Early intervention: coma stimulation in the intensive care unit. J Neurosci Nurs. 1994 December; 26(6): 336–341; Mitchell S, et al. Coma arousal procedure: a therapeutic intervention in the treatment of head injury. Brain Inj. 1990 July; 4(3): 273–279. Wood R L, et al. Evaluating sensory regulation as a method to improve awareness in patients with altered states of consciousness: a pilot study. Brain Inj. 1992 September; 6(5): 411–418.). Sensory stimulation achieves excitation of such areas as the reticular formation, lemniscal pathways, specific and non-specific and cortical regions. Using the ABS, sensory stimulation parameters including intensity, duration, and frequency can be modified and the corresponding resultant present state compared to a reference state in order to choose the optimum stimulation parameters for creating cortical excitation. Sensory stimulation may be combined with DBS's to maximize induced arousal by stimulating the brain by two different means.

Currently, the brainstem auditory evoked potential (BAEP) and somatosensory evoked potential (SSEP) are considered valuable diagnostic means to determine the probability that a patient will successfully recover from coma and regain consciousness. By defining a present state, estimated by qualifying the BAEP, SSEP, EEG or EMG during the post-stimulus period, and comparing it to an appropriate reference state, the clinical efficacy of a set of parameters for peripheral stimuli can be evaluated and changed if necessary to aid in recovery of patients from coma.

Additionally, the ABS system and method of the present invention can be used in the treatment of sensory disorders by sensory aids that stimulate the CNS or sensory pathway, such as a multi-channel implantable neural stimulator which functions as an auditory prosthesis. By comparing the present EP to a sensor input to a reference EP obtained from a past sensor input the stimulation parameters of an implanted device can be set to achieve the optimum performance from the implanted stimulator.

Additionally, the ABS system and method of the present invention can be used in the treatment of movement disorders such as Parkinson's Disease by stimulation of the CNS or motor pathway, where the present state is computed primarily from EMG data and is compared to a reference state and the stimulation parameters are changed according to the result of this comparison so that the stimulation parameters ultimately used are of maximum benefit to a patient.

The presently described embodiments of the adaptive brain stimulation system and method are based upon 3 components: stimulation, comparison of a present state with a reference state, and subsequent stimulation that is contingent upon the results of the comparison. Although modifications and changes may be suggested by those skilled in the art, it is the intention of the inventors to embody within the patent warranted herein all changes and modifications as reasonably and properly come within the scope of their contribution to the art.

What is claimed is:

1. An adaptive brain stimulation device for treating brain disorder or disfunction comprising:
   a. a sensing means including a sensor or a set of sensors for sensing data used to compute a present state of a patient,
   b. stimulating means for stimulating a first brain region of the central nervous system of said patient according to a first set of stimulation parameters,
   c. comparator means for making a statistical comparison operation between said present state and a reference state, said comparison operation resulting in a positive outcome or a negative outcome,
   e. means for adjusting said stimulation parameters according to the outcome of said comparing said present state to said reference state.

2. An adaptive brain stimulation device of claim 1 in which said present state is at least one quantitative measurement that is computed from physiological data that are sensed by at least one sensor, which is implanted within or is external to a patient, said data being sensed during a period of active stimulation or at least one fraction of said period of active stimulation, or during a post-stimulation period, or at least a fraction of said post-stimulation period.

3. An adaptive brain stimulation device of claim 1 in which said present state is computed from physiological data sensed by at least one a sensor which is implanted internally within or are located externally to a patient.

4. An adaptive brain stimulation device of claim 1 wherein said reference state is a set of values selected from a database which contains at least one of the following: a previous state of said patient, a weighted sum of previous states, a population normative value in a normal state, or under the influence of a pharmacological agent, or a weighted state computed based upon evidence of neuronal damage or other physiological, neuro-anatomical, or neuropharmacological characteristics of said patient.

5. An adaptive brain stimulation device of claim 1 wherein said comparison operation is performed between said present state and said reference state, said comparison operation being accomplished in the time domain or in the frequency domain, or on a user defined or calculated threshold value or on a set of threshold values, said comparison operation using a set of statistical criteria and a set of medically meaningful weighting coefficients that may be chosen by medical personnel or which can be selected from a database.

6. An adaptive brain stimulation device of claim 1 wherein stimulating means for stimulating a first brain region comprises a direct brain stimulator set #1, said direct brain stimulator set #1 being comprised of at least one direct brain stimulator.

7. An adaptive brain stimulation device of claim 6 wherein the direct brain stimulator set #1 comprises multiple direct brain stimulators, each being independently activated, and subsequently independently controlled by separate said stimulating parameters.

8. An adaptive brain stimulation device of claim 1 wherein said stimulation parameters include but are not limited to at least pulse amplitude, pulse width, onset and offset times, frequency, a burst firing mode and a non-burst firing mode, AM and FM pulse train type, DC offset, pulse current, polarity, pulse duration, and inter-pulse interval.

9. An adaptive brain stimulation device of claim 1 in which said present state and said reference state are each computed from at least one quantitative measurement that is computed from physiological data that are sensed by said sensing means, said sensing means including at least one sensor located inside of a patient or located fully external to a patient.

10. An adaptive brain stimulation device of claim 1 in which said means for sensing a state includes a sensor which is at least one of the following: an internally implanted electrode, a conventional scalp EEG electrode, an EMG electrode, an EKG electrode, a pet scanner, a spect scanner, an MRI scanner, an FMRI scanner.

11. An adaptive brain stimulation device of claim 1 in which means for stimulation is at least one of the following: an electrical means, a magnetic means, or a pharmacological means.

12. An adaptive brain stimulation device of claim 1 in which said means for stimulation comprises either direct stimulation or induced stimulation.

13. An adaptive brain stimulation device of claim 1 which additionally contains safety means for monitoring the autonomic nervous system and for halting said stimulation means if any of a set of vital signs exceeds a value which is deemed to be medically unsafe.

14. An adaptive brain stimulation device of claim 1 in which said means for stimulation includes devices for stimulation of the visual, auditory, or tactile sensory modalities.

15. A method of using the neurological stimulation device of claim 1 which additionally includes detecting a present state that is characterized by certain rhythmic or non-rhythmic change in a subjects temperature, eye movement, EMG, neurochemical (CSF metabolites), or neural activity and only enabling possible stimulation when said rhythmic or non-rhythmic change is detected.

16. An adaptive brain stimulation device comprising:
   a. means for sensing a present state of at least a first brain region, or a fist set of brain regions and a second brain region or a second set of brain regions,
   b. means for stimulating a first brain region or a first set of brain regions by a direct brain stimulator set #1 according to a first set of stimulation parameters,
   c. means for stimulating a second brain region or a second set of brain regions by a direct brain stimulator set #2 according to a second set of stimulation parameters,
   d. means for comparing said present state to a reference state, said comparing leading to a positive outcome or a negative outcome, e. means for adjusting said stimulation parameters according to the outcome of said comparing said present and said reference state.

17. An adaptive brain stimulation device of claim 17 in which said means for stimulation comprises an electrical, magnetic, or pharmacological stimulation means.

18. An adaptive brain stimulation device of claim 17 in which said present state is during a period of active stimulation, during a post-stimulation period or a fraction of said period which occurs prior to or subsequent to said period of active stimulation.

19. An adaptive brain stimulation device of claim 17 in which said present state is computed from at least one quantitative measurement that is computed from data sensed by at least one sensor which is implanted internally within or are located externally to a patient, and are compared to a self norm or a population norm.

20. An adaptive brain stimulation device of claim 17 wherein said reference state is a set of values selected from a database, and is a previous state of said patient, a weighted sum of previous states, a population normative value in a normal state, or under the influence of a pharmacological agent.

21. An adaptive brain stimulation device of claim 17 wherein the means for comparing said present state to said reference state is a statistical comparison operation which may be univariate or multivariate.

22. An adaptive brain stimulation device of claim 17 wherein DBS set #1 is comprised of at least one DBS.

23. An adaptive brain stimulation device of claim 17 wherein DBS set #1 is comprised of multiple DBS's which may each be independently activated, and subsequently independently controlled by different said stimulation parameters.

24. An adaptive brain stimulation device of claim 17 wherein said stimulation parameters include but are not limited to pulse amplitude, pulse width, onset and offset times, frequency, a burst firing mode or a non-burst firing mode, AM or FM pulse train type, DC offset, pulse current, inter-pulse interval, relative polarity, and relative latency.

25. A method of using adaptive brain stimulation in the treatment of brain disorder or disfunction which comprises:

a. sensing the present state of several brain regions, stimulating a first brain region or a first set of brain regions according to a set of stimulation parameters, c. performing a statistical comparison between the present state and a reference table, d. changing said stimulation parameters if the comparison fails to meet a criteria, and e. repeating steps a, b, c, and d.

26. A method of claim 25 which additionally includes the step of stimulating a second brain region or a second set of brain regions if the comparison succeeds in a meeting a criteria.

27. A method of claim 25 which additionally includes the step of providing positive reinforcement by stimulating at least a second brain region if the comparison succeeds in meeting a criteria.

28. A method of treating Parkinson's Disease and other movement disorders which comprises:

a. sensing the present state of one or more brain regions and/or peripheral regions, b. stimulating a first brain region or a first set of brain regions according to a set of stimulation parameters, c. performing a statistically significant comparison between the present state and a reference state, d. changing said stimulation parameters if the comparison fails to meet a criteria, and e. repeating steps a, b, c, and d.

29. A method of claim 28 which additionally includes the step of stimulating a second brain region or a second set of brain regions if the comparison succeeds in meeting a criteria.

30. A method of claim 28 in which the medically significant comparison includes assigning relatively large weighting coefficients to the sensing of said peripheral regions said sensing being accomplished by conventionally located EMG electrodes.

* * * * *